(12) United States Patent
Lin

(10) Patent No.: US 10,881,762 B2
(45) Date of Patent: *Jan. 5, 2021

(54) METHOD FOR MANUFACTURING BIOINDUCTIVE PATCH

(71) Applicant: DE NOVO ORTHOPEDICS INC., Taipei (TW)

(72) Inventor: Chia-Wei Lin, Kaohsiung (TW)

(73) Assignee: DE NOVO ORTHOPEDICS INC., Taipei (TW)

(*) Notice: Subject to any disclaimer, the term of this patent is extended or adjusted under 35 U.S.C. 154(b) by 147 days.

This patent is subject to a terminal disclaimer.

(21) Appl. No.: 16/190,102

(22) Filed: Nov. 13, 2018

(65) Prior Publication Data

US 2019/0142997 A1 May 16, 2019

Related U.S. Application Data

(60) Provisional application No. 62/586,651, filed on Nov. 15, 2017.

(51) Int. Cl.
*A61L 27/58* (2006.01)
*A61L 27/36* (2006.01)
*A61L 27/34* (2006.01)
*A61L 27/54* (2006.01)
*A61L 27/38* (2006.01)
(Continued)

(52) U.S. Cl.
CPC .......... *A61L 27/58* (2013.01); *A61B 17/0401* (2013.01); *A61F 2/30756* (2013.01); *A61L 27/24* (2013.01); *A61L 27/34* (2013.01); *A61L 27/3604* (2013.01); *A61L 27/3662* (2013.01); *A61L 27/3691* (2013.01); *A61L 27/3843* (2013.01); *A61L 27/54* (2013.01); *A61B 2017/044* (2013.01); *A61B 2017/0404* (2013.01); *A61B 2017/0414* (2013.01); *A61F 2002/2817* (2013.01); *A61F 2002/30751* (2013.01); *A61F 2002/30761* (2013.01); *A61K 31/765* (2013.01); *A61L 2300/414* (2013.01); *Y10T 29/49826* (2015.01)

(58) Field of Classification Search
CPC .. A61L 27/58; A61L 27/3604; A61L 27/3662; A61L 27/3691; A61L 27/34; A61L 27/54; A61L 27/3843; A61L 27/24; A61L 2300/414; A61F 2/30756; A61F 2002/30761; A61F 2002/2817; A61F 2002/30751; A61B 17/0401; A61B 2017/0404; A61B 2017/0414; A61B 2017/044; A61K 31/765; Y10T 29/49826
See application file for complete search history.

(56) References Cited

U.S. PATENT DOCUMENTS 4,467,479 A * 8/1984 Brody .................. A61B 17/562
128/898
4,667,675 A * 5/1987 Davis ................. A61B 17/0466
24/71.1

(Continued)

*Primary Examiner* — Sarang Afzali
(74) *Attorney, Agent, or Firm* — ScienBiziP, P.C.

(57) ABSTRACT

A bioinductive patch includes a patch body and a button. The patch body has an inner space. The button is disposed in the inner space of the patch body. A method for manufacturing a bioinductive patch includes step in which a patch body having an inner space is provided. The method continues with step in which a button is disposed in the inner space of the patch body.

13 Claims, 9 Drawing Sheets

(51) Int. Cl.
*A61L 27/24* (2006.01)
*A61F 2/30* (2006.01)
*A61B 17/04* (2006.01)
*A61K 31/765* (2006.01)
*A61F 2/28* (2006.01)

(56) References Cited

U.S. PATENT DOCUMENTS

| | | | | |
|---|---|---|---|---|
| 4,755,184 A * | 7/1988 | Silverberg | A61F 2/28 | 433/201.1 |
| 5,344,459 A * | 9/1994 | Swartz | A61F 2/3872 | 623/14.12 |
| 5,456,721 A * | 10/1995 | Legrand | A61F 2/08 | 623/1.5 |
| 6,110,210 A * | 8/2000 | Norton | A61F 2/441 | 623/17.16 |
| 6,264,695 B1 * | 7/2001 | Stoy | A61F 2/441 | 623/17.16 |
| 6,533,817 B1 * | 3/2003 | Norton | A61F 2/0095 | 623/17.11 |
| 6,733,533 B1 * | 5/2004 | Lozier | A61F 2/441 | 606/247 |
| 6,746,483 B1 * | 6/2004 | Bojarski | A61B 17/0401 | 623/13.14 |
| 7,001,390 B2 * | 2/2006 | Gebhardt | A61F 2/0811 | 606/151 |
| 7,241,316 B2 * | 7/2007 | Evans | A61L 27/58 | 623/23.51 |
| 7,279,008 B2 * | 10/2007 | Brown | A61B 17/0401 | 623/13.13 |
| 7,503,936 B2 * | 3/2009 | Trieu | A61F 2/441 | 623/17.16 |
| 7,722,895 B1 * | 5/2010 | McKay | A61L 27/227 | 424/423 |
| 8,012,211 B2 * | 9/2011 | Kuslich | A61F 2/442 | 623/17.12 |
| 8,070,700 B2 * | 12/2011 | Kazerooni | A61F 5/00 | 602/16 |
| 8,177,841 B2 * | 5/2012 | Ek | A61F 2/30756 | 623/14.12 |
| 8,267,973 B2 * | 9/2012 | Humphrey | A61B 17/0401 | 606/232 |
| 8,623,085 B2 * | 1/2014 | Gatt | A61F 2/30756 | 623/14.12 |
| 8,864,827 B2 * | 10/2014 | Ek | A61F 2/30756 | 623/14.12 |
| 8,900,620 B2 * | 12/2014 | Fulmer | A61M 31/002 | 424/426 |
| 9,034,052 B2 * | 5/2015 | Shimko | A61F 2/2846 | 623/23.52 |
| 9,138,219 B2 * | 9/2015 | Horrell | A61B 17/0401 | |
| 9,381,683 B2 * | 7/2016 | Armbruster | A61L 27/50 | |
| 9,526,668 B2 * | 12/2016 | Goffer | B25J 9/0006 | |
| 9,579,260 B2 * | 2/2017 | Fulmer | A61B 17/8028 | |
| 10,111,696 B2 * | 10/2018 | Voisard | A61L 27/34 | |
| 10,639,161 B2 * | 5/2020 | Makower | A61F 2/3836 | |
| 2002/0026244 A1 * | 2/2002 | Trieu | A61F 2/4611 | 623/17.16 |
| 2002/0055749 A1 * | 5/2002 | Esnouf | A61F 2/08 | 606/148 |
| 2002/0077701 A1 * | 6/2002 | Kuslich | A61F 2/442 | 623/17.12 |
| 2002/0128713 A1 * | 9/2002 | Ferree | A61F 2/4611 | 623/17.11 |
| 2003/0078617 A1 * | 4/2003 | Schwartz | A61F 2/30749 | 606/230 |
| 2003/0135209 A1 * | 7/2003 | Seedhom | A61B 17/1659 | 606/60 |
| 2003/0195628 A1 * | 10/2003 | Bao | A61F 2/442 | 623/17.12 |
| 2004/0143333 A1 * | 7/2004 | Bain | A61L 27/52 | 623/17.16 |
| 2004/0143344 A1 * | 7/2004 | Malaviya | A61L 27/18 | 623/23.72 |
| 2004/0199249 A1 * | 10/2004 | Fell | A61F 2/3872 | 623/14.12 |
| 2006/0241765 A1 * | 10/2006 | Burn | A61F 2/441 | 623/17.12 |
| 2007/0038301 A1 * | 2/2007 | Hudgins | A61F 2/441 | 623/17.16 |
| 2007/0093906 A1 * | 4/2007 | Hudgins | A61F 2/441 | 623/17.16 |
| 2007/0100450 A1 * | 5/2007 | Hodorek | A61L 27/52 | 623/14.12 |
| 2008/0004714 A1 * | 1/2008 | Lieberman | A61F 2/00 | 623/23.76 |
| 2008/0172125 A1 * | 7/2008 | Ek | A61F 2/3859 | 623/14.12 |
| 2008/0262630 A1 * | 10/2008 | Fulmer | A61J 3/00 | 623/23.52 |
| 2009/0076605 A1 * | 3/2009 | Linares | A61F 2/28 | 623/14.12 |
| 2009/0187252 A1 * | 7/2009 | Howald | A61B 17/562 | 623/22.15 |
| 2009/0306778 A1 * | 12/2009 | Marvel | A61F 2/30756 | 623/14.12 |
| 2010/0023126 A1 * | 1/2010 | Grotz | A61F 2/30721 | 623/14.12 |
| 2010/0168771 A1 * | 7/2010 | Guldberg | A61L 27/52 | 606/151 |
| 2010/0292798 A1 * | 11/2010 | Maestretti | A61F 2/441 | 623/17.12 |
| 2011/0288642 A1 * | 11/2011 | Forsell | A61F 2/3872 | 623/14.12 |
| 2013/0116794 A1 * | 5/2013 | Shohat | A61F 2/30756 | 623/19.11 |
| 2013/0312897 A1 * | 11/2013 | Vowles | A61B 6/50 | 156/83 |
| 2014/0128974 A1 * | 5/2014 | Bromer | A61F 2/30721 | 623/14.12 |
| 2014/0155944 A1 * | 6/2014 | Truman | A61B 17/8061 | 606/324 |
| 2014/0222149 A1 * | 8/2014 | Amis | A61F 2/3872 | 623/14.12 |
| 2017/0000473 A1 * | 1/2017 | Benedict | A61F 2/30756 | |
| 2017/0224498 A1 * | 8/2017 | McCullen | A61F 2/30767 | |
| 2018/0028320 A1 * | 2/2018 | Forsell | A61F 2/3601 | |
| 2018/0360610 A1 * | 12/2018 | Patel | A61F 2/442 | |
| 2019/0262496 A1 * | 8/2019 | Zender | A61L 27/54 | |
| 2019/0343642 A1 * | 11/2019 | Koenen | A61F 2/3872 | |
| 2020/0060834 A1 * | 2/2020 | McCullen | A61F 2/3872 | |

* cited by examiner

METHOD FOR MANUFACTURING BIOINDUCTIVE PATCH

CROSS-REFERENCE TO RELATED APPLICATIONS

This application claims the benefit of U.S. Provisional Application No. 62/586,651, filed Nov. 15, 2017, the entire disclosure of which is incorporated by reference herein.

FIELD

The disclosure relates to a method for manufacturing a patch, more particular to a method for manufacturing a bioinductive patch.

BACKGROUND

Rotator cuff tear is one of the most common tendon disorders, which is often caused by chronic wear and tear with degeneration of the tendon. Rotator cuff tear can also occur in people who repeatedly perform overhead motions in their jobs or sports. According to statistics, approximately 13% of the population at an age greater than 50 suffers from rotator cuff tear, and over half of the population at an age greater than 80 is diagnosed with a rotator cuff tendon injury.

Treatment of the rotator cuff tear often includes surgical repair, but the rate of failure to gain or maintain healing has been reported to be as high as over 90%. This has been substantially attributed to the inadequate capacity of rotator cuff to heal once damaged. Scaffolds have been developed to improve rotator cuff-bone healing and rotator cuff regeneration, but not possess durable biological characteristics and ideal healing rate.

SUMMARY OF THE INVENTION

In accordance with one aspect of the present disclosure, a bioinductive patch includes a patch body and a button. The patch body has an inner space. The button is disposed in the inner space of the patch body.

In accordance with another aspect of the present disclosure, a method for manufacturing a bioinductive patch includes step in which a patch body having an inner space is provided. The method continues with step in which a button is disposed in the inner space of the patch body.

BRIEF DESCRIPTION OF THE DRAWINGS

Aspects of the present disclosure are understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION OF THE INVENTION

Figure 1:
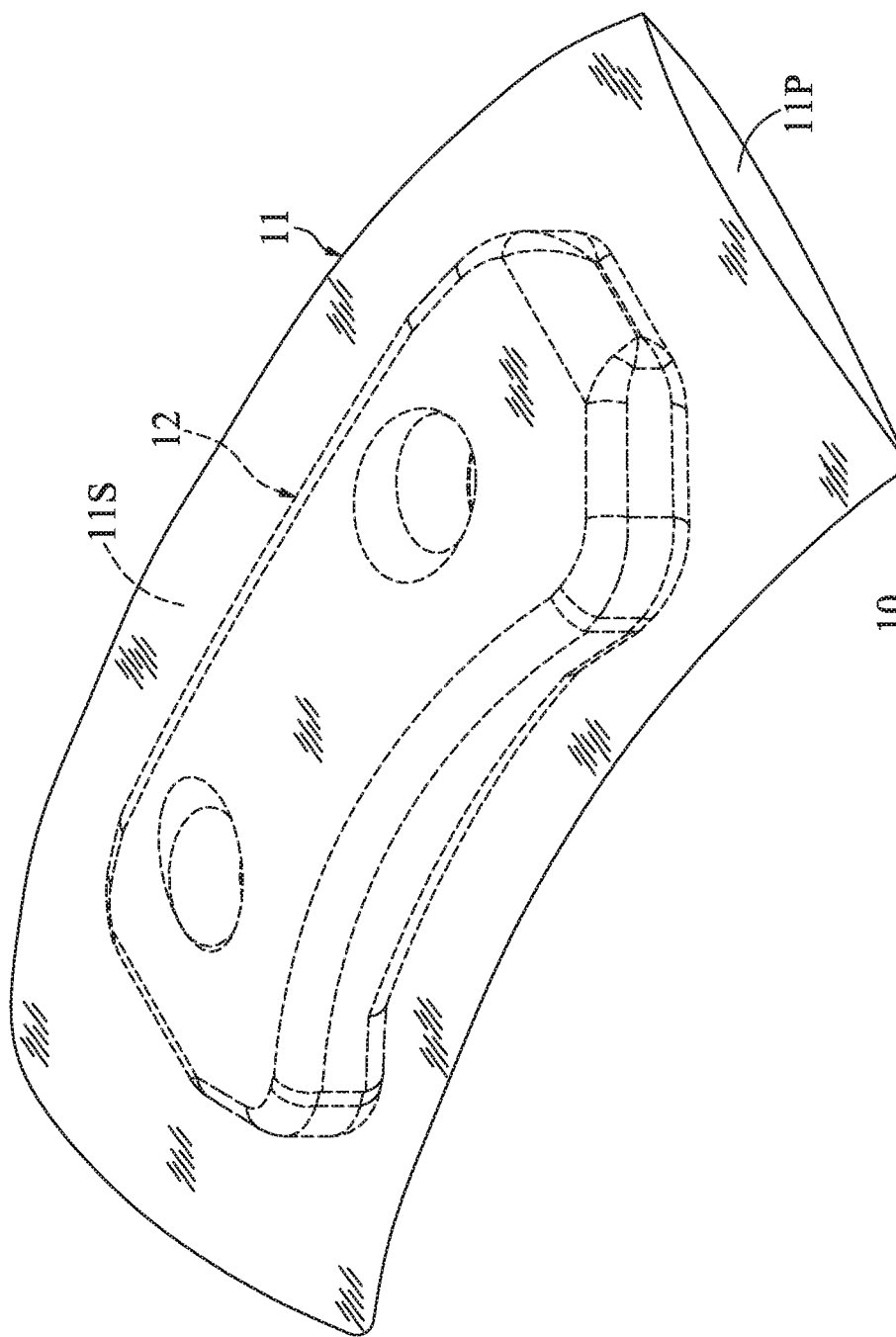
FIG. 1 is a perspective view of a bioinductive patch in accordance with some embodiments of the present disclosure.

It is to be understood that the following disclosure provides many different embodiments or examples, for implementing different features of various embodiments. Specific examples of components and arrangements are described below to simplify the present disclosure. The present disclosure may, however, be embodied in many different forms and should not be construed as being limited to the embodiments set forth herein; rather, these embodiments are provided so that this description will be thorough and complete, and will fully convey the present disclosure to those of ordinary skill in the art. It will be apparent, however, that one or more embodiments may be practiced without these specific details.

In addition, the present disclosure may repeat reference numerals and/or letters in the various examples. This repetition is for the purpose of simplicity and clarity and does not in itself dictate a relationship between the various embodiments and/or configurations discussed.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
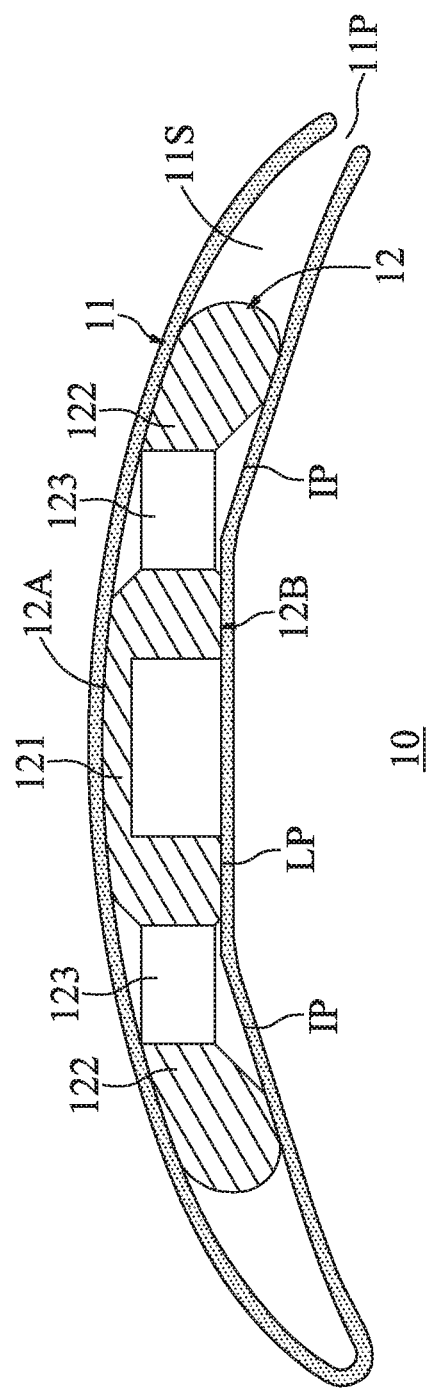
FIG. 2 is a cross-sectional view of a bioinductive patch in accordance with some embodiments of the present disclosure.
Figure 3:
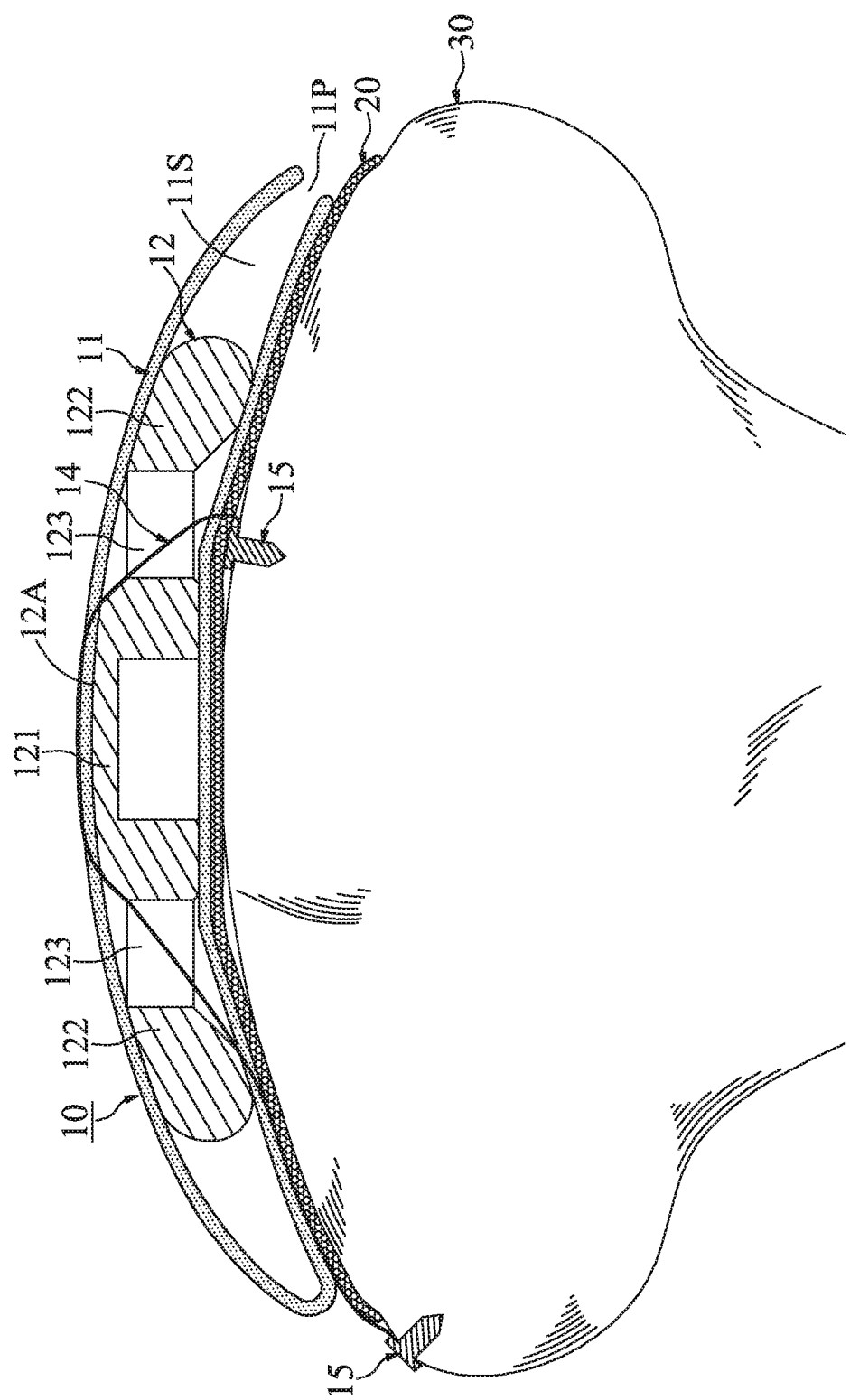
FIG. 3 illustrates a cross-sectional view of a bioinductive patch for reattaching a biological tissue to a hard tissue in accordance with some embodiments of the present disclosure.

Referring to FIGS. 1-3, a bioinductive patch 10 is designed to be placed on a biological tissue 20. In some embodiments, the biological tissue 20 is a soft tissue such as rotator cuff. In some embodiments, the biological tissue 20 can also be a hard tissue such as the bone chip. In some embodiments, the bioinductive patch 10 is used to help detatched biological tissue 20 (as rotator cuff) heal onto a hard tissue 30 (as humerus).

The bioinductive patch 10 includes a patch body 11 and a button 12. The patch body 11 is made of bioabsorbable material. In some embodiments, the bioabsorbable material is decellularized collagen or amniotic membrane which can provide an environment that promotes the biological tissue 20 healing and regeneration.

The patch body 11 has an inner space 11S and an opening 11P. The inner space 11S is in communication with the opening 11P. In the present embodiment, the patch body 11 is in envelope shape.

The button 12 is disposed in the inner space 11S of the patch body 11 through the opening 11P.

Figure 4:
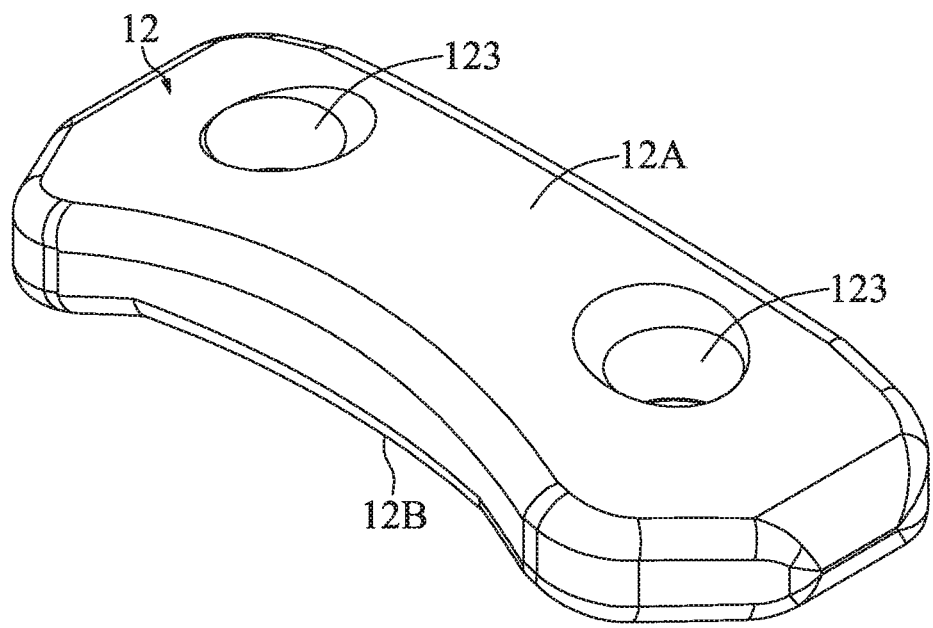
FIG. 4 is a perspective view of a button in accordance with some embodiments of the present disclosure.
Figure 5:
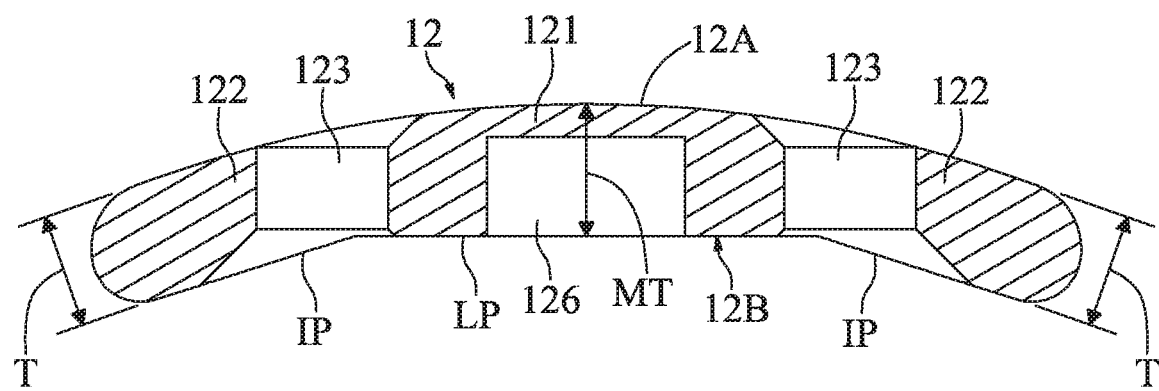
FIG. 5 is a cross-sectional view of a button in accordance with some embodiments of the present disclosure.

Referring to FIGS. 2, 4 and 5, the button 12 has a top surface 12A, a bottom surface 12B, a central portion 121, two side curved portions 122, and two suture holes 123.

The top surface 12A contacts the patch body 11. In the present embodiment, the top surface 12A is an arc surface to match the geometry of the hard tissue.

Figure 6:
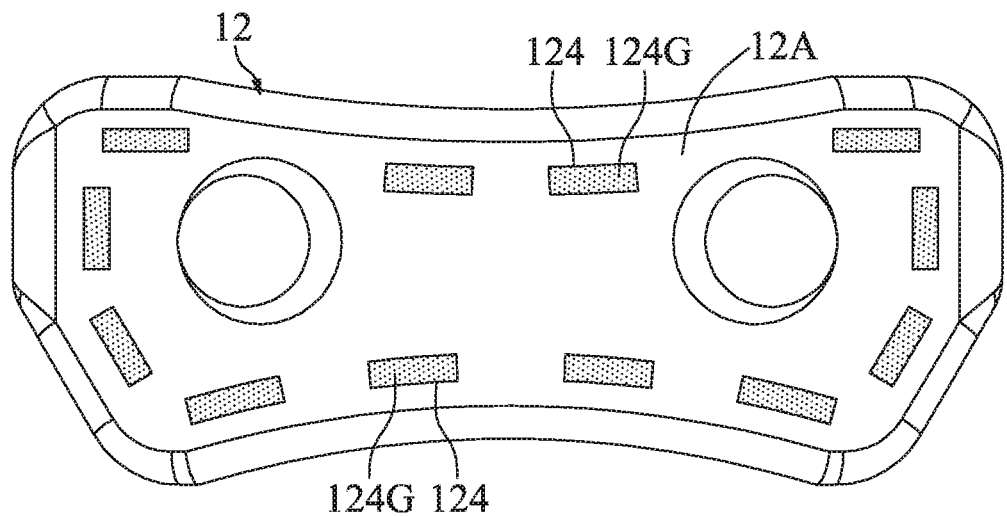
FIG. 6 is a top view of a button in accordance with some embodiments of the present disclosure.

Referring to FIGS. 3 and 6, in order to enhance the elasticity of the button 12, the button 12 can have a plurality of top cavities 124 formed on the top surface 12A. In some embodiments, the top cavities 124 can be disposed with at least one growth factor 124G. The growth factor 124G can be bonded and retained to the patch body 11.

Referring to FIGS. 2, 4 and 5 again, the bottom surface 12B contacts the patch body 11. In the present embodiment, the bottom surface 12B includes a level plane LP and two inclined planes IP. The level plane LP is located at the central portion 121. The two inclined planes IP are located at two sides of the level plane LP, respectively.

Figure 7:
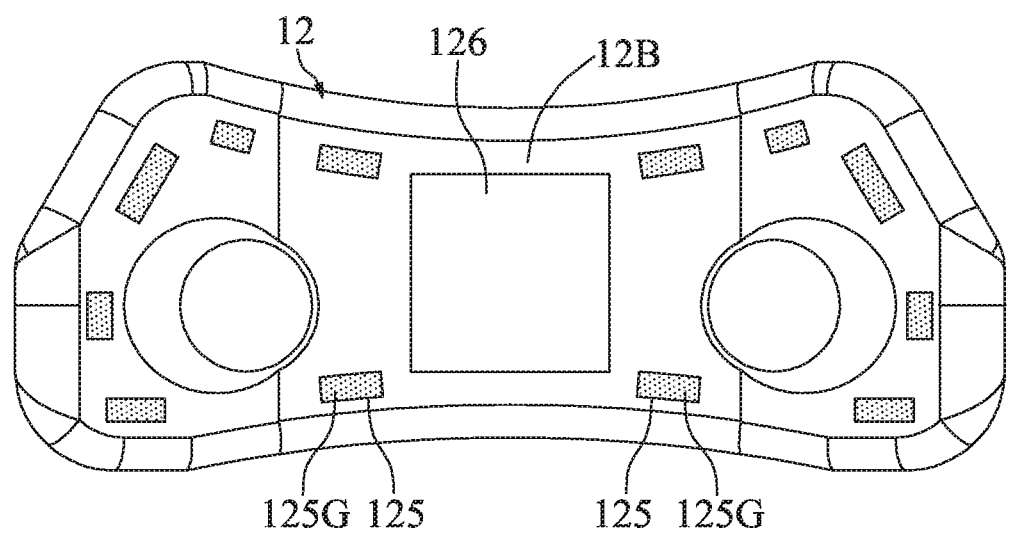
FIG. 7 is a bottom view of a button in accordance with some embodiments of the present disclosure.

Referring to FIGS. 3 and 7, in order to enhance the elasticity of the button 12, the button 12 can have a plurality of bottom cavities 125 formed on the bottom surface 12B. In some embodiments, the bottom cavities 125 can be disposed with at least one growth factor 125G. The growth factor 125G can bond to the patch body 11 and be retained inside the cavities.

Referring to FIG. 5 again, the central portion 121 has a center maximum thickness MT to increase overall stiffness and avoid breakage.

The two side curved portions 122 are connected to two sides of the central portion 121, respectively. In the present embodiment, the center maximum thickness MT of the central portion 121 is greater than or equal to a thickness T of the side curved portion 122 to ensure that the button 12 can have a sufficient bending strength.

Referring to FIGS. 2, 3 and 5 again, the two suture holes 123 are formed at the two side curved portions 122, respectively. At least one suture 14 can penetrate the two suture holes 123 to press the button 12 and the patch body 11 on the biological tissue 20. In the present embodiment, the at least one suture 14 is secured to suture anchors 15 or the tunnel inside the hard tissue 30, and the suture anchors 15 are configured to fix on the hard tissue 30.

Figure 8:
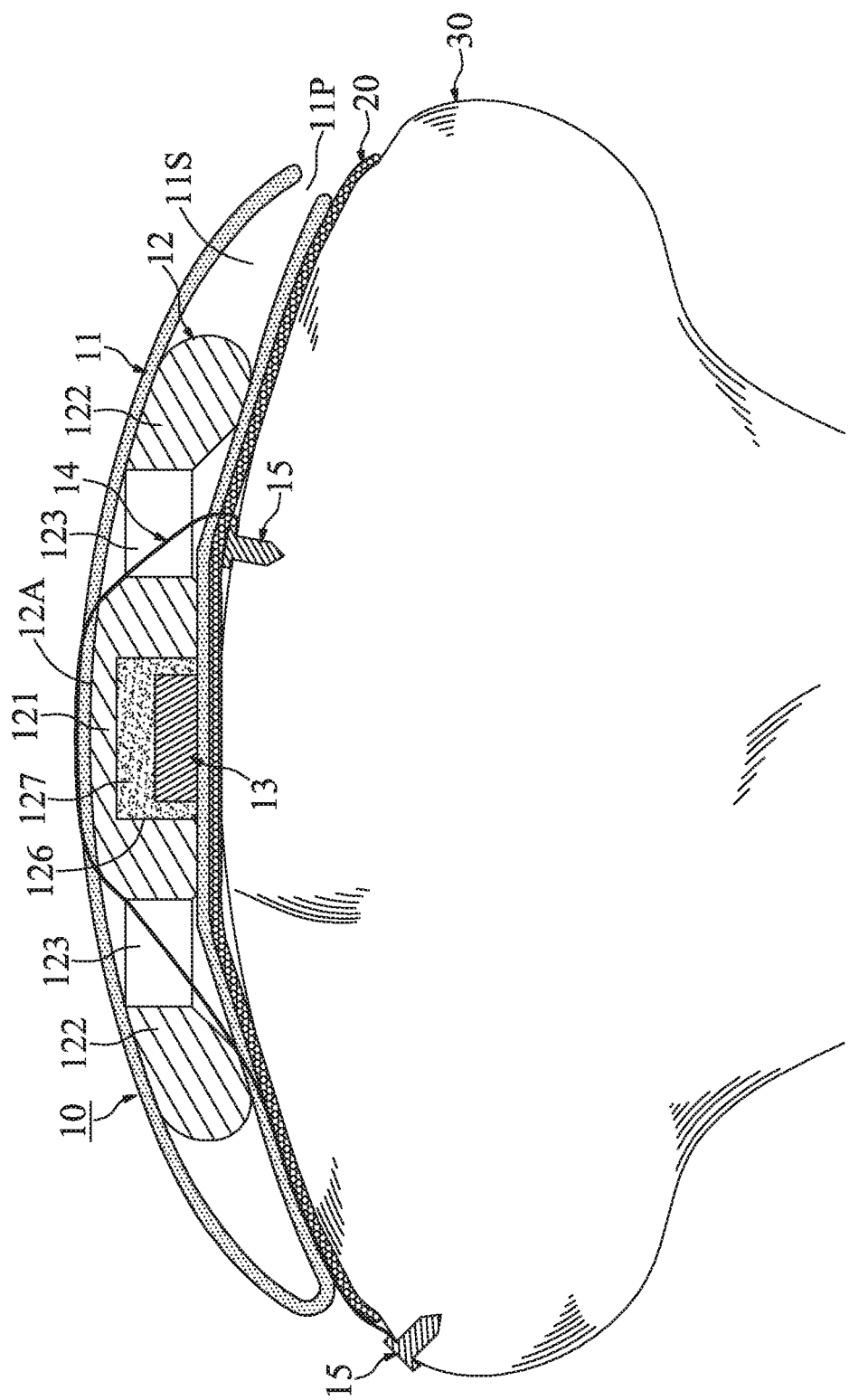
FIG. 8 illustrates a cross-sectional view of a bioinductive patch with a force sensor for reattaching a biological tissue to a hard tissue in accordance with some embodiments of the present disclosure.

Referring to FIGS. 3 and 8, a force sensor 13 can be disposed on the button 12 to detect a force variation between the button 12 and the biological tissue 20. The force sensor 13 can be pressure sensor, shear force sensor or tensile force sensor. Accordingly, the force variation can be pressure variation, shear force variation or tensile force variation.

In the present embodiment, the button 12 has a bottom recession 126 dented from the bottom surface 12B and located at the central portion 121. The force sensor 13 is disposed in the bottom recession 126. Preferably, the force sensor 13 does not protrude from the bottom recession 126. In some embodiments, the bottom recession 126 can be filled with a sealing material 127 to seal the force sensor 13.

To improve the accuracy of the detected force variation, the force sensor 13 is located between the two suture holes 123.

According to above configurations, the bioinductive patch 10 of the present invention can effectively improve biological tissue-hard tissue healing and possess durable biological characteristics.

Figure 9:
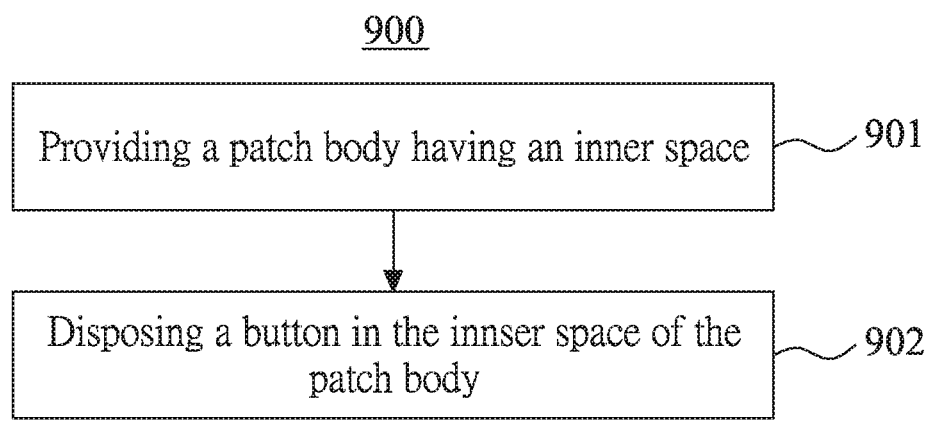
FIG. 9 is a flow diagram illustrating a method for manufacturing a bioinductive patch in accordance with some embodiments of the present disclosure.

Referring to FIG. 9, a method 900 includes step 901 in which a patch body is provided, wherein the patch body has an inner space.

Figure 10A:
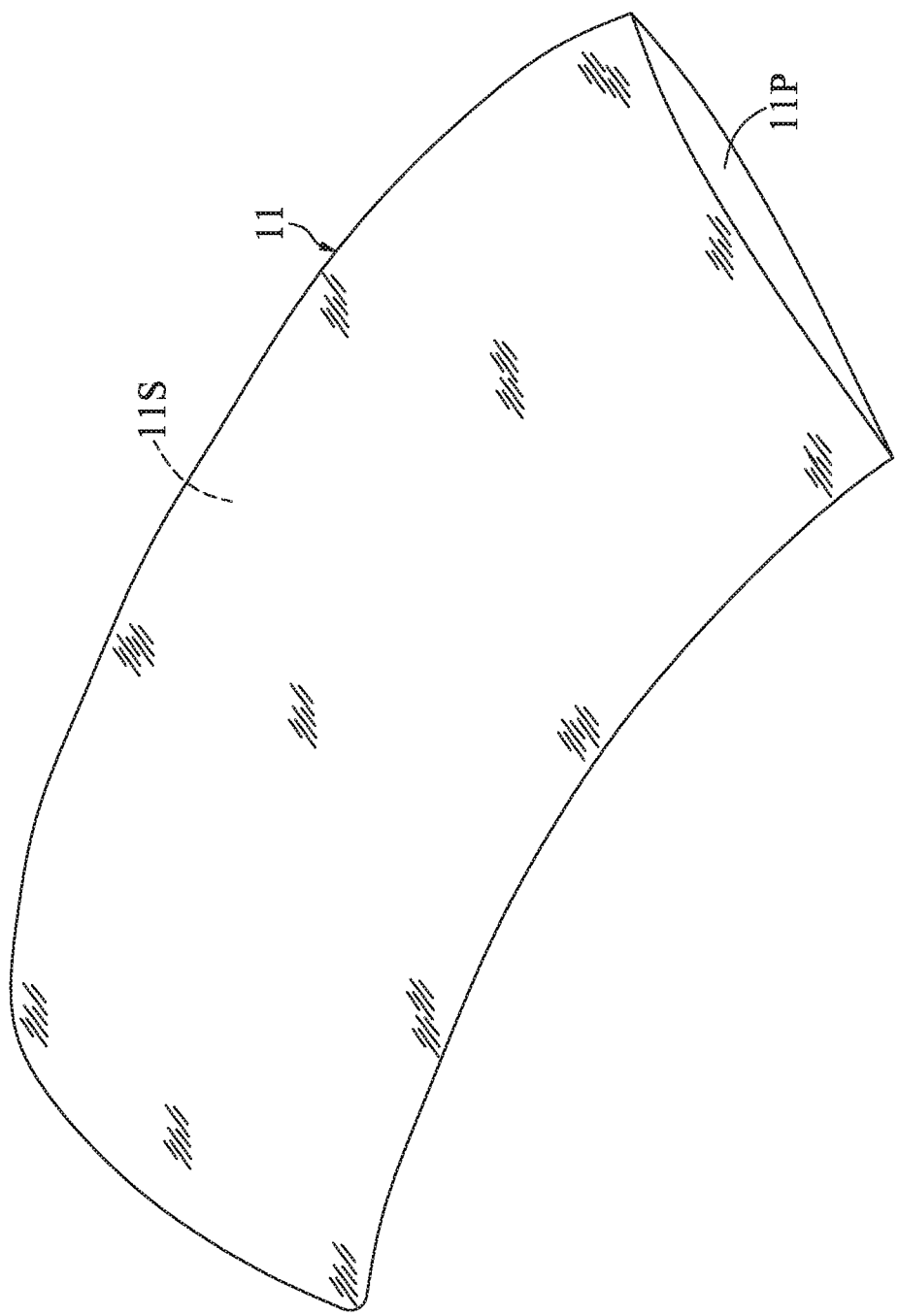
FIG. 10A illustrates a schematic view of a patch body corresponding to the step 901 of FIG. 9.

In FIG. 10A, a patch body 11 is provided. The patch body 11 is made of decellularized material. In some embodiments, the material is decellularized bioinductive collagen or amniotic membrane which can provide an environment that promotes the biological tissue healing and regeneration.

The patch body 11 has an inner space 11S and an opening 11P. The inner space 11S is in communication with the opening 11P. In the present embodiment, the patch body 11 is in envelope shape.

Referring to FIG. 9 again, the method 900 continues with step 902 in which a button is disposed in the inner space of the patch body.

Figure 10B:
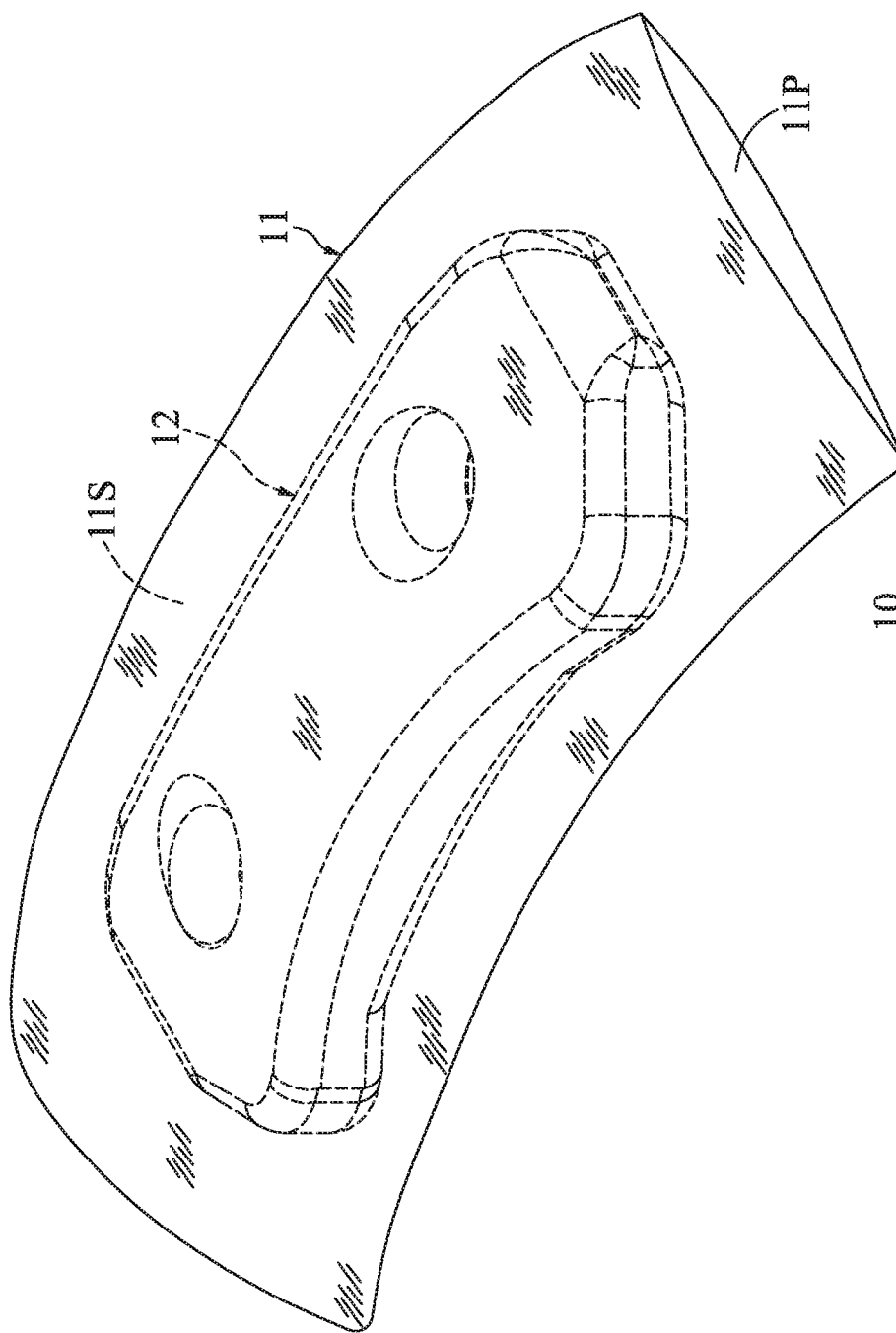
FIG. 10B illustrates a schematic view of a button disposed in the patch body corresponding to the step 902 of FIG. 9.

In FIG. 10B, a button 12 is disposed in the inner space 11S of the patch body 11 through the opening 11P, to form the bioinductive patch 10.

Referring to FIGS. 2, 4 and 5 again, the button 12 has a top surface 12A, a bottom surface 12B, a central portion 121, two side curved portions 122, and two suture holes 123.

The top surface 12A contacts the patch body 11. In the present embodiment, the top surface 12A is an arc surface to match the geometry of the hard tissue.

Referring to FIGS. 3 and 6 again, in order to enhance the elasticity of the button 12, the button 12 can have a plurality of top cavities 124 formed on the top surface 12A. In some embodiments, the top cavities 124 can be disposed with at least one growth factor 124G. The growth factor 124G can be bonded and retained to the patch body 11.

Referring to FIGS. 2, 4 and 5 again, the bottom surface 12B contacts the patch body 11. In the present embodiment, the bottom surface 12B includes a level plane LP and two inclined planes IP. The level plane LP is located at the central portion 121. The two inclined planes IP are located at two sides of the level plane LP, respectively.

Referring to FIGS. 3 and 7 again, in order to enhance the elasticity of the button 12, the button 12 can have a plurality of bottom cavities 125 formed on the bottom surface 12B. In some embodiments, the bottom cavities 125 can be disposed with at least one growth factor 125G. The growth factor 125G can bond to the patch body 11 and be retained inside the cavities.

Referring to FIG. 5 again, the central portion 121 has a center maximum thickness MT to increase overall stiffness and avoid breakage.

The two side curved portions 122 are connected to two sides of the central portion 121, respectively. In the present embodiment, the center maximum thickness MT of the central portion 121 is greater than or equal to a thickness T of the side curved portion 122 to ensure that the button 12 can have a sufficient bending strength.

Referring to FIGS. 2, 3 and 5 again, the two suture holes 123 are formed at the two side curved portions 122, respectively. At least one suture 14 can penetrate the two suture holes 123 to press the button 12 and the patch body 11 on the biological tissue 20. In the present embodiment, the at least one suture 14 is secured to suture anchors 15 or the tunnel inside the hard tissue 30, and the suture anchors 15 are configured to fix on the hard tissue 30.

Referring to FIGS. 3 and 8 again, a force sensor 13 can be disposed on the button 12 to detect a force variation between the button 12 and the biological tissue 20. The force sensor 13 can be pressure sensor, shear force sensor or tensile force sensor. Accordingly, the force variation can be pressure variation, shear force variation or tensile force variation.

In the present embodiment, the button 12 has a bottom recession 126 dented from the bottom surface 12B and located at the central portion 121. The force sensor 13 is disposed in the bottom recession 126. Preferably, the force sensor 13 does not protrude from the bottom recession 126. In some embodiments, the bottom recession 126 can be filled with a sealing material 127 to seal the force sensor 13.

To improve the accuracy of the detected force variation, the force sensor 13 is located between the two suture holes 123.

The above method of the present invention includes only two steps, which has the advantages of short manufacture period and low manufacturing cost.

Moreover, the scope of the present application is not intended to be limited to the particular embodiments of the process, machine, manufacture, and composition of matter, means, methods and steps described in the specification. As those skilled in the art will readily appreciate form the present disclosure, processes, machines, manufacture, compositions of matter, means, methods, or steps, presently existing or later to be developed, that perform substantially the same function or achieve substantially the same result as the corresponding embodiments described herein may be utilized in accordance with some embodiments of the present disclosure.

Accordingly, the appended claims are intended to include within their scope such processes, machines, manufacture, and compositions of matter, means, methods or steps. In addition, each claim constitutes a separate embodiment, and the combination of various claims and embodiments are within the scope of the invention.

What is claimed is:

1. A method for manufacturing a bioinductive patch, the method comprising:
   providing a patch body having an inner space and an opening; and
   disposing a button in the inner space of the patch body through the opening, wherein the button has a central portion and two side curved portions and the two side curved portions are connected to two sides of the central portion, respectively to form the bioinductive patch, wherein the patch body is made of decellularized bioinductive collagen or amniotic membrane, wherein the bioinductive patch is configured to be placed on and conform to a biological tissue to promote healing and regeneration of the biological tissue.

2. The method of claim 1, wherein the button has a bottom surface contacting the patch body.

3. The method of claim 2, wherein the button has a plurality of bottom cavities formed on the bottom surface.

4. The method of claim 3, wherein the bottom cavities are disposed with at least one growth factor.

5. The method of claim 2, wherein the bottom surface comprises a level plane and two inclined planes, and the two inclined planes are located at two sides of the level plane, respectively.

6. The method of claim 1, wherein the button has a top surface contacting the patch body.

7. The method of claim 6, wherein the button has a plurality of top cavities formed on the top surface.

8. The method of claim 7, wherein the top cavities are disposed with at least one growth factor.

9. The method of claim 1, further comprising disposing a force sensor on the button.

10. The method of claim 9, wherein the button has a bottom surface and a bottom recession dented from the bottom surface, and the force sensor is disposed in the bottom recession.

11. The method of claim 10, wherein the force sensor does not protrude from the bottom recession.

12. The method of claim 1, wherein a center maximum thickness of the central portion is greater than or equal to a thickness of at least one of the two side curved portions.

13. The method of claim 1, wherein the button has two suture holes formed at the two side curved portions, respectively.

* * * * *